(12) United States Patent
Edwards et al.

(10) Patent No.: US 6,881,828 B2
(45) Date of Patent: Apr. 19, 2005

(54) FUSION PROTEINS BETWEEN ANTIGENIC AMINO ACID SEQUENCES AND BETA-2-MICROGLOBULIN

```
ATGTTCTCTCCAATTTTGTCCTTGGAAATTATTTTAGCTTTGGCTACTTTGCAATCTGTCTTCGCTATCCAGCGTACTCC
TACAAGAGAGGTTAAAACAGGAACCTTTAATAAAATCGAAACCGATGAAACGTTAGACAGAAGCGATAGGTCGCATGAGG
▶MetPheSerProIleLeuSerLeuGluIleIleLeuAlaLeuAlaThrLeuGlnSerValPheAlaIleGlnArgThrPr

AAAGATTCAGGTTTACTCACGTCATCCAGCAGAGAATGGAAAGTCAAATTTCCTGAATTGCTATGTGTCTG
TTTCTAAGTCCAAATGAGTGCAGTAGGTCGTCTCTTACCTTTCAGTTTAAAGGACTTAACGATACACAGAC
▶oLysIleGlnValTyrSerArgHisProAlaGluAsnGlyLysSerAsnPheLeuAsnCysTyrValSerG

GGTTTCATCCATCCGACATTGAAGTTGACTTACTGAAGAATGGAGAGAGAATTGAAAAAGTGGAGCATTCA
CCAAAGTAGGTAGGCTGTAACTTCAACTGAATGACTTCTTACCTCTCTCTTAACTTTTTCACCTCGTAAGT
▶lyPheHisProSerAspIleGluValAspLeuLeuLysAsnGlyGluArgIleGluLysValGluHisSer

EcoRI
GACTTGTCTTTCAGCAAGGACTGGTCTTTCTATCTCTTGTACTACACTGAATTCACCCCCACTGAAAAAGA
CTGAACAGAAAGTCGTTCCTGACCAGAAAGATAGAGAACATGATGTGACTTAAGTGGGGGTGACTTTTTCT
▶AspLeuSerPheSerLysAspTrpSerPheTyrLeuLeuTyrTyrThrGluPheThrProThrGluLysAs

TGAGTATGCCTGCCGTGTGAACCATGTGACTTTGTCACAGCCCAAGATAGTTAAGTGGGATCGAGACATGT
ACTCATACGGACGGCACACTTGGTACACTGAAACAGTGTCGGGTTCTATCAATTCACCCTAGCTCTGTACA
▶pGluTyrAlaCysArgValAsnHisValThrLeuSerGlnProLysIleValLysTrpAspArgAspMet-
    BamHI (609)
AATAAGGATCC
TTATTCCTAGG
▶ · · · · ·
```

FUSION PROTEINS BETWEEN ANTIGENIC AMINO ACID SEQUENCES AND BETA-2-MICROGLOBULIN

This invention concerns novel hybrid beta-2 microglobulin fusion proteins. It also relates to nucleic acid (DNA and RNA) coding for all or part of such proteins, and to their preparation. Pharmaceutical compositions containing such fusion proteins are useful both as components of prophylactic vaccines and as immuno-therapeutics for the post-exposure treatment of viral infection and malignancy.

Immune responses have two major components, humoral and cell-mediated. The first comprises antibodies, produced by B-lymphocytes, which bind to specific antigens and which serve a number of important functions such as neutralization of viruses, complement fixation and immune complex formation. Antibody production is dependent on helper T cells, which mediate the antigen specific recognition of peptide epitopes displayed by Class II Major Histocompatibility Complex (MHC) molecules on the surface of antigen presenting cells.

The second arm of the immune system involves effector T cells, in particular cytotoxic T lymphocytes (CTLs) which can recognize and kill infected or transformed cells. Such responses are particularly important in the defense against and immunity from viral infections, though they are also involved in host responses against certain tumours. CTL responses are also antigen specific, involving subsets of CD8 positive T cells. Immune recognition is mediated by the T cell receptor which recognizes the peptide antigen displayed on Class I MHC molecules.

Class I MHC molecules are ubiquitously expressed and consist of two polypeptide chains. The first is an alpha chain of about 45 kDa comprising 3 domains. Two of these domains bind to peptides derived from processing endogenously synthesized proteins, such as viral components, and present them to the T cell receptor. These two domains are linked to a single membrane spanning anchor region by a third, immunoglobulin-like domain. The second component is beta-2 microglobulin (B2M), a 100 amino acid protein which can exist free in the serum as well as a part of Class I MHC. The two chains normally associate in the ER, along with peptides produced by the degradation of endogenous proteins to form a ternary complex which is displayed on the cell surface. Although binary complexes lacking peptide can be formed, these are unstable and are normally recycled or degraded (Ljungren et al. Nature 346, 476-(1990).

Crystallographic data reveals that the antigenic peptide binds to a groove between the first two domains of the alpha subunit, the base of which is formed from strands of beta sheet, and the walls from two alpha helices (Biorkman et al. Nature 329, 506–512 (1987)). The nature of the side chains in this region of the alpha chain are critical in determining the peptide selectivity of the molecule, and hence the ability of different Class I MHC alleles to respond to particular epitopes (Bjorkman et al. Nature 329, 512–518 (1987)). Although it is the alpha subunit that binds the peptide, B2M plays an essential role in allowing binding, presumably by stabilising the ternary complex (Vitiello et al. Science 250, 1423–1426 (1990); Rock et al. PNAS 88, 310–304 (1991)). While some free alpha subunit can reach the cell surface in the absence of B2M, and can bind and present peptide, it is considerably less efficient than in the presence of B2M (Bix and Raulet. Exp. Med. 176, 829–834 (1992).

Although the normal route of antigen presentation by Class I MHC involves the degradation of endogenously synthesised proteins, it is possible to achieve antigen presentation by addition of high concentrations of peptide to antigen presenting cells (APC) in vitro. The use of peptides as immunogens has a number of potential advantages, the most significant of which are that it avoids the use of inactivated or attenuated viral particles, and that small peptides can be synthesised chemically, avoiding the requirement for biological production routes. The most efficient presentation is obtained with peptides of from 9–11 residues in length, which corresponds to the length of the groove if they are in an extended conformation.

However, there are major problems associated with this method of eliciting a CTL response. Although such a use of peptides is adequate for demonstrating immune responses such as T cell-mediated killing in vitro, it is not an efficient process, and does not offer a practical route to in vivo immunization. CTL responses may be induced by immunization with certain small peptide fragments but such peptides may elicit poor antibody responses. Further, in an outbred population, individuals of different MHC class I and class II haplotypes will respond to different peptide epitopes; many peptides may be required to prime all the possible haplotypes.

Most of the available evidence also indicates that immunization with whole proteins does not give rise to a CTL response. Such CTL responses that have been induced require the presence of powerful adjuvants or live vector which have not been licensed for use in humans. For example, recombinant HIV gp160 presented in ISCOMs, but not in FCA, FIA or buffered saline, induced HIV-1 envelope-specific CTL activity in BALB/c mice. It is generally felt that approval for the use of ISCOMs in humans is unlikely to be forthcoming. Recombinant vaccinia viruses expressing the V3 region of the HIV envelope gp160 also induce specific CTL responses to the V3 region, but immunization with vaccinia has raised concerns both about safety for immunocompromised patients, and about efficacy. A simpler and more efficient way to induce CTL responses is therefore an important goal, and has been sought actively for a number of years though with only limited success.

It has been shown that the exchange of B2M chains in MHC class I will occur in the presence of free B2M (Hayfil and Strominger, PNAS USA 76(11) 5834–5838 (1979)), and that the binding of exogenous peptides to these molecules occurs upon association and reassociation of B2M light chains (Rock et al., PNAS USA 87 7517–7521 (1990); Kozlowski et al. Nature 349, 74–77 (1991)). The presentation of exogenously added peptide can therefore be made more efficient by the addition of B2M. The use of exogenous B2M in this way to enhance immune responses against peptides in vivo is described in WO-A-91/16924.

However, there are a number of problems with this approach. The use of an admixture, while a convenient tool for in vitro use, is less appropriate for in vivo administration, due to the problems of polypharmacy for product registration.

Further, despite the DNA sequence of B2M being known, it has not been possible to produce recombinant B2M efficiently. B2M for use in the enhancement of immune responses would therefore need to be purified from natural sources such as serum or urine. Not only is this difficult and expensive, but blood products must be screened for a number of contaminants before being acceptable for use in vaccines.

Despite the fact that interactions between the C-terminus of the peptide and the alpha subunit have been shown to be essential for peptide binding and presentation, the present invention has found that peptides fused to the N-terminus of B2M are still capable of binding to the groove in the alpha subunit. This binding is achieved without sacrificing the ability of the ternary complex to bind and trigger the T-cell receptor.

According to the first aspect of the invention there is provided a hybrid fusion protein comprising a first antigenic amino acid sequence fused to a second amino acid sequence substantially homologous with B2M or a fragment thereof.

Preferably the first antigenic sequence is fused to the B2M sequence via a short linker sequence, to span the gap between the peptide and the B2M with minimal disruption to the conformation of the light chain.

The use of B2M fusions offers considerable advantages. The binary complex between the alpha subunit and the B2M fusion is stabilised relative to the corresponding ternary complex, prolonging the ability of the peptide to stimulate the T cell receptor, thereby increasing the effective potency of the peptide. The problems of polypharmacy are avoided, simplifying the development of the compound. This approach also has a number of product registration advantages by minimising the number of proteins present in the vaccine, and may conform more closely to guidelines on quality and safety. Finally, only a single GMP production route is required. These latter considerations are particularly important since multiple epitopes might be required to produce a vaccine effective against the background of MHC diversity. A final advantage is that because the peptide is delivered efficiently to the MHC, the requirement for adjuvants may be obviated.

The expression "substantially homologous", when describing the relationship of an amino acid sequence to a natural protein, means that the amino acid sequence can be identical to the natural protein or can be an effective but truncated or modified form of the natural protein. As a practical matter, though, most analogues will have a high degree of homology with the prototype molecule if biological activity is to be substantially preserved. It will be realised that the nature of changes from the prototype molecule is more important than the amount of them. As guidance, though, at the amino acid level, it may be that at least 60%, 70%, 80%, 90%, 95% or even 99% of the residues will be the same as the prototype molecule; at the nucleic acid level, nucleic acid coding for an analogue may for example hybridize under stringent conditions (such as at approximately 35° C. to 65° C. in a salt solution of approximately 0.9 molar) to nucleic acid coding for the prototype molecule, or would do so but for the degeneracy of the genetic code.

Fragments of B2M for use in this invention will retain the ability to augment immune responses to the peptides to which they are fused. Preferably at least 60%, 70%, 80%, 90%, 95% or even 99% of the residues will be retained.

Proteins substantially homologous to B2M include naturally occurring B2M and modified B2M, a variant found in connection with a variety of types of cancer and disorders of the immune system.

The antigenic sequence may correspond to a sequence derived from or associated with an aetiological agent or a tumor. The aetiological agent may be a microorganism such as a virus, bacterium, fungus or parasite. The virus may be: a retrovirus, such as HIV-1, HIV-2, HTLV-I, HTLV-II, HTLV-III, SIV, BIV, LAV, EIAV, CIAV, murine leukaemia virus, Moloney murine leukaemia virus, and feline leukaemia virus; an orthomyxovirus, such as influenza A or B; a paramyxovirus, such as parainfluenza virus, mumps, measles, RSV and Sendai virus; a papovavirus, such as HPV; an arenavirus, such as LCMV of humans or mice; a hepadnavirus, such as Hepatitis B virus; a herpes virus, such as HSV, VZV, CMV, or EBV. HIV is human immunodeficiency virus, HTLV is human T-cell lymphoma leukemia virus, SIV is simian immunodeficiency virus, BIV is bovine immunodeficiency virus, LAV is lymphadenopathy associated virus, EIAV is equine infectious anemia virus, CIAV is chicken infectious anemia virus, RSV is respiratory syncytial virus, HPV is human papilloma virus, LCMV is lymphocytic choriomeningitis virus, HSV is herpes simplex virus, VZV is varicella zoster virus, CMV is cytomegalovirus, and EBV is Epstein Barr virus. The tumor-associated or derived antigen may for example be a proteinaceous human tumor antigen, such as a melanoma-associated antigen, or an epithelial-tumor associated antigen such as from breast or colon carcinoma.

The antigenic sequence may be also derived from a bacterium, such as of the genus *Neisseria, Campilobacter, Bordetella, Listeria, Mycobacteria* or *Leishmania*, or a parasite, such as from the genus *Trypanosoma, Schizosoma, Plasmodium*, especially *P. falciparum*, or from a fungus, such as from the genus *Candida, Aspergillus, Cryptococcus, Histoplasma* or *Blastomyces.*

Preferred antigenic sequences correspond to CTL epitopes from a retrovirus, a paramyxovirus, an arenavirus or a hepadna virus, or a human tumor cell.

Examples include epitopes from:

1) HIV (particularly HIV-1) gp120,
2) HIV (particularly HIV-1) p24
3) VZV gpI, gpII and gpIII
4) LCMV nucleoprotein,
5) Influenza virus nucleoprotein,
6) HPV L1 and L2 proteins,
7) Human papilloma virus E5 and E7
8) Malaria CSP or RESA antigens,
9) Mycobacterium p6,
10) GA 733-2 epithelial tumor-associated antigen,
11) MUC-1 repeat sequence from epithelial tumor-associated antigen,
12) Melanoma MZ2-E antigens
13) Melanoma p97 associated antigen, Particularly preferred antigenic sequences are derived from the third variable domain of an envelope protein of a lentivirus. This region of lentiviruses, known as the V3 loop or GPGR loop is found between amino acids 300 and 330 of gp120 of HIV-1 and in analogous positions of other lentiviruses. The V3 loop is, for HIV-1 at least, the major neutralising epitope of the virus (Putney et al 1986 *Science* 234, 1392; Rusche et al 1988 *Proc. Natl. Acad. Sci.* 85, 3198; Palker et al 1988 *Proc. Natl. Acad. Sci.* 85 1932; and Goudsmit et al., 1988 *AIDS* 2 157). The antigenic portion of choice may constitute the whole of the V3 loop when derived from different strains. However, multiple copies of a conserved sequence of the V3 loop may be useful in conferring immunity against more than one isolate of a virus (such as HIV-1).

B2M fusion proteins in accordance with the invention can in principle be made by any convenient method including coupling successive amino acid residues together, or by the chemical coupling of two or more oligo- or polypeptide chains or of existing (for example natural) proteins. Although proteins may in principle be synthesised wholly or partly by chemical means, the route of choice will be ribosomal translation, preferably in vivo, of a corresponding nucleic acid sequence.

According to a second aspect of the invention, therefore, there is provided nucleic acid coding for a fusion protein as described above. Both DNA and RNA are within the scope of the invention. DNA may be chemically synthesized and/or recombinant.

Recombinant DNA in accordance with the invention may be in the form of a vector. The vector may for example be a plasmid, cosmid or phage. Vectors will frequently include one or more selectable markers to enable the selection of cells transformed (or transfected: the terms are used interchangeably in this specification) with them and, preferably, to enable selection of cells harboring vectors incorporating heterologous DNA. Appropriate translational initiating and termination signals will generally be present. Additionally, if the vector is intended for expression, sufficient transcriptional regulatory sequences to drive expression will be included. Vectors not including regulatory sequences are useful as cloning vectors. According to a third aspect of the invention there is provided a vector including nucleic acid as described above. It is to be understood that the term "vector" is used in this specification in a functional sense and is not to be construed as necessarily being limited to a single nucleic acid molecule.

Expression vectors in accordance with the invention will usually contain a promoter. The nature of the promoter will depend upon the intended host expression cell. For yeast, PGK is a preferred promoter, but any other suitable promoter may be used if necessary or desirable. Examples include GAPD, GAL1–10, PH05, ADH1, CYC1, Ty delta sequence, PYK and hybrid promoters made from components from more than one promoter (such as those listed). For insect cells, a preferred promoter is the polyhedrin promoter from *Autographica californica* nuclear polyhedrosis virus (AcNPV). Those skilled in the art will be able to determine other appropriate promoters adapted for expression in these or other cells. Vectors not including promoters may be useful as cloning vectors, rather than expression vectors.

Cloning vectors can be introduced into *E. coli* or any other suitable hosts which facilitate their manipulation. Expression vectors may be adapted for prokaryotic expression in bacterial cells, such as *E. coli*. However, for preference vectors are adapted for expression in a microbial eukaryotic cell, such as a yeast (including but not limited to *Saccharomyces cerevisiae* and *Pichia pastoris*) or a higher eukaryotic cell such as insect cell lines such as *Spodoptera frugiperda* SF9, or mammalian cells including Chinese hamster ovary (CHO) cells, mouse myeloma cell lines such as P3X63-Ag8.653, COS cells, HeLa cells, BHK cells, melanoma cell lines such as the Bowes cell line, mouse L cells, human hepatoma cell lines such as Hep G2, mouse fibroblasts and mouse NIH 3T3 cells. Performance of the invention is neither dependent on nor limited to any particular strain of microorganism or cell type: those suitable for use with the invention will be apparent to those skilled in the art, following the teaching of this specification. According to a fourth aspect of the invention there is provided a host cell transfected or transformed with DNA described above.

Despite the DNA sequence of B2M being known, to date it has not been possible to produce recombinant B2M efficiently. Extremely low yields are produced by expression in mammalian cells, and the protein is incorrectly folded following expression in *E. coli*. Nor are yeasts a universal host for the purpose. Standard techniques for obtaining expression of B2M in perhaps the most widely used yeast for such purposes, namely *S. cerevisiae*, resulted in very poor yields.

The *Pichia pastoris* expression system is well known, and has particular advantages in its ease of scalability for large scale production. High level expression has been obtained for a number of proteins in that host, but equally, some have proved difficult to produce. There is no obvious correlation between the properties of a particular polypeptide and its ability to be highly expressed in the *Pichia* system.

In contrast with the low level expression of B2M in *S. cerevisiae*, reasonable yields of the fusion proteins of this invention can be obtained in the *Pichia* system.

Therefore, the invention includes a method of producing fusion proteins of the invention by cultivating a methylotropic yeast harbouring an expression vector comprising DNA encoding the relevant fusion protein, and recovering the expressed fusion protein.

Methylotropic yeast strains include *Pichia*, in particular *P. pastoris*, *Hansenula*, *Candida* and *Torulopsis*. Use of *Pichia pastoris* is presently preferred.

Recombinant DNA encoding the fusion proteins of the invention may be incorporated in a yeast expression vector for expression in methylotropic yeast in accordance with the invention. Such vectors will usually contain a promoter. AOX is a preferred promoter, but any other suitable promoter may be used if necessary or desirable. Examples include GAPD, GAL1–10, PH05, ADH1, PGK, CYC1, Ty delta sequence, PYK and hybrid promoters made from components from more than one promoter (such as those listed).

To obtain secretion of the fusion protein from the yeast cells after expression, the expression vector preferably includes a secretion leader sequence fused to the B2M sequence of the hybrid fusion protein. After secretion, the leader sequence is automatically cleaved from the B2M protein by enzyme(s) produced naturally during the cultivation of the transformed yeast cells. Such secretion techniques are well known. Secretion leaders known to the art include the alpha factor, Pho1, HSA and Suc2. If cleavage is not 100% accurate, the final yield of fusion protein may be contaminated with a fusion of B2M/epitope hybrid with part of the secretion factor sequence, indicating incomplete removal of the secretion factor leader. Although the hybrid protein of the invention may be separated from the contaminant by standard purification methods, for example those based on differing molecular weights, it would be desirable to avoid the difficulty if possible.

It appears the Pho1 leader is in general correctly cleaved from the hybrid fusion proteins of the invention, and it is therefore the presently preferred secretion factor for use in accordance with the invention.

The B2M fusion proteins of the first aspect are useful as vaccines. These might be used prior to exposure as prophylactic agents, or after exposure as immunotherapeutic agents to enhance the clearance of viral infection. Such fusion proteins would be administered by conventional routes, either i.v., i.m. or s.c., though the s.c. route may be preferred.

According to a fifth aspect of the invention, there is provided a pharmaceutical or veterinary formulation comprising a compound of general formula I and a pharmaceutically or veterinarily acceptable carrier. One or more fusion proteins of the first aspect may be present in association with one or more non-toxic pharmaceutically or veterinarily acceptable carriers such as sterile physiological saline or sterile PBS, and/or diluents and/or adjuvants and if desired other active ingredients. Sterility will generally be essential for parenterally administrable vaccines. One or more appropriate adjuvants may also be present. Examples of suitable adjuvants include muramyl peptide compounds such as prototype muramyl dipeptide, aluminium hydroxide and saponin. Coadministration with cytokines may also be considered, eg IFNγ may potentiate the immune response by inducing class I MHC expression.

It may be preferred that, when used as prophylactic vaccines, the B2M agents are used in combination with subunit vaccines designed to induce good neutralising antibody responses. However, this may not be necessary as there is some evidence that CTL responses alone can protect against infection.

According to a sixth aspect of the invention, there is provided a process for the preparation of a pharmaceutical or veterinary formulation in accordance with the fifth aspect, the process comprising admixing a B2M fusion protein of the first aspect and a pharmaceutically or veterinarily acceptable carrier.

The active ingredient may be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Particulate antigens produced in accordance with the invention may be useful in the preparation of vaccines, for example immunotherapeutic vaccines, which form a further aspect of the invention.

The following Example illustrate the invention

EXAMPLE 1

Isolation of the B2M Gene and Preparation for Cloning

RNA was purified from human blood cells using the isothiocyanate guanidinium method (RNAzol B™, Biogenesys). This RNA was used as the template for synthesis of first strand cDNA with the use of oligo dT primers using the method of Maniatis (in Molecular Cloning, 1989).

Figures 2, 3, 4:
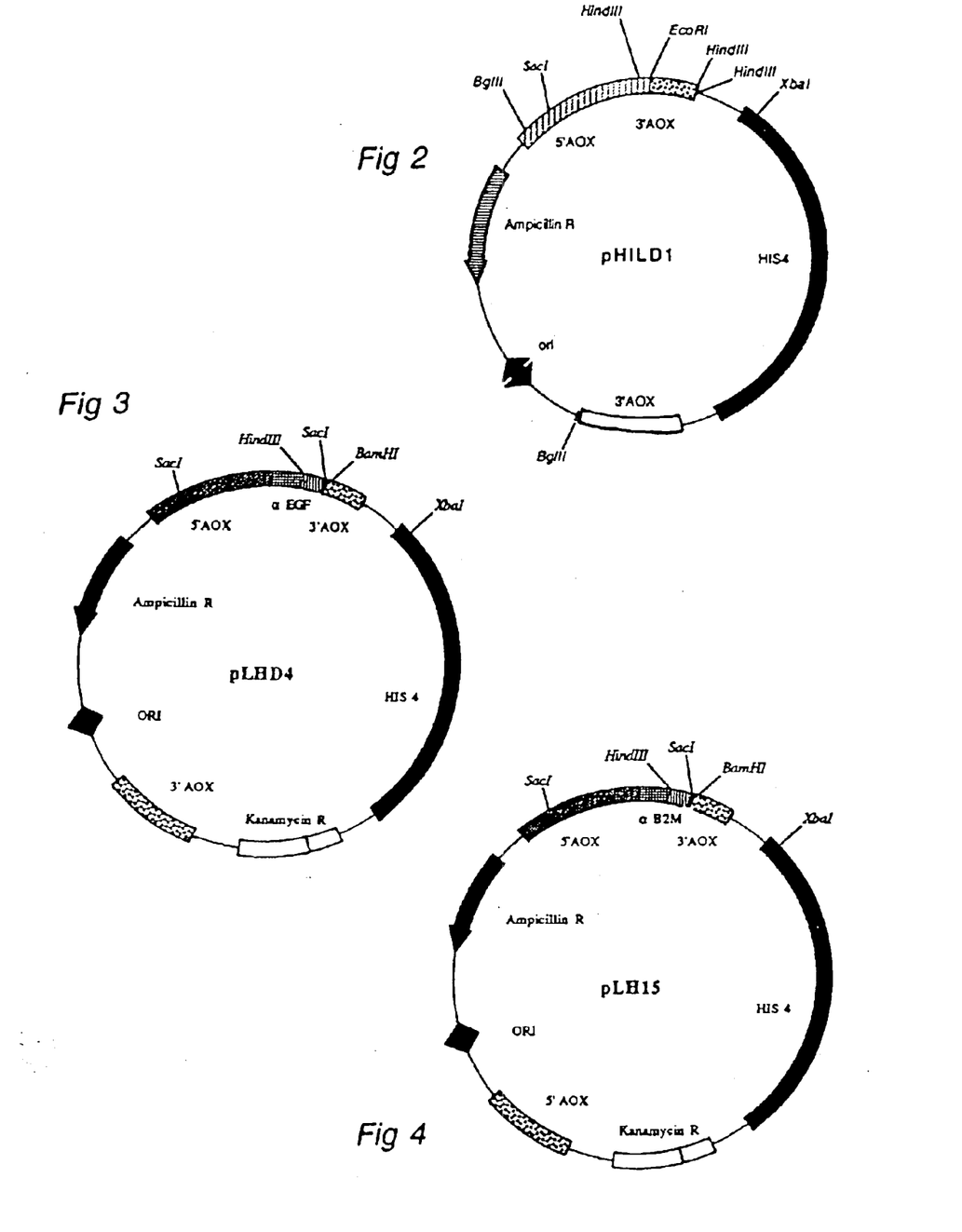
FIG. 2 shows the *Pichia* expression vector pHILD1 used as the starting point in example 3 for the construction of the expression vector for high-level expression of B2M in *P.pastoris*, using the alpha factor leader sequence.
FIG. 3 shows the intermediate vector pLHD4 used in example 3 in the construction of the *P. pastoris* alpha factor/B2M expression vector.
FIG. 4 shows the *P. pastoris* alpha factor/B2M expression vector pLH15 prepared according to example 3.
Figure 5:
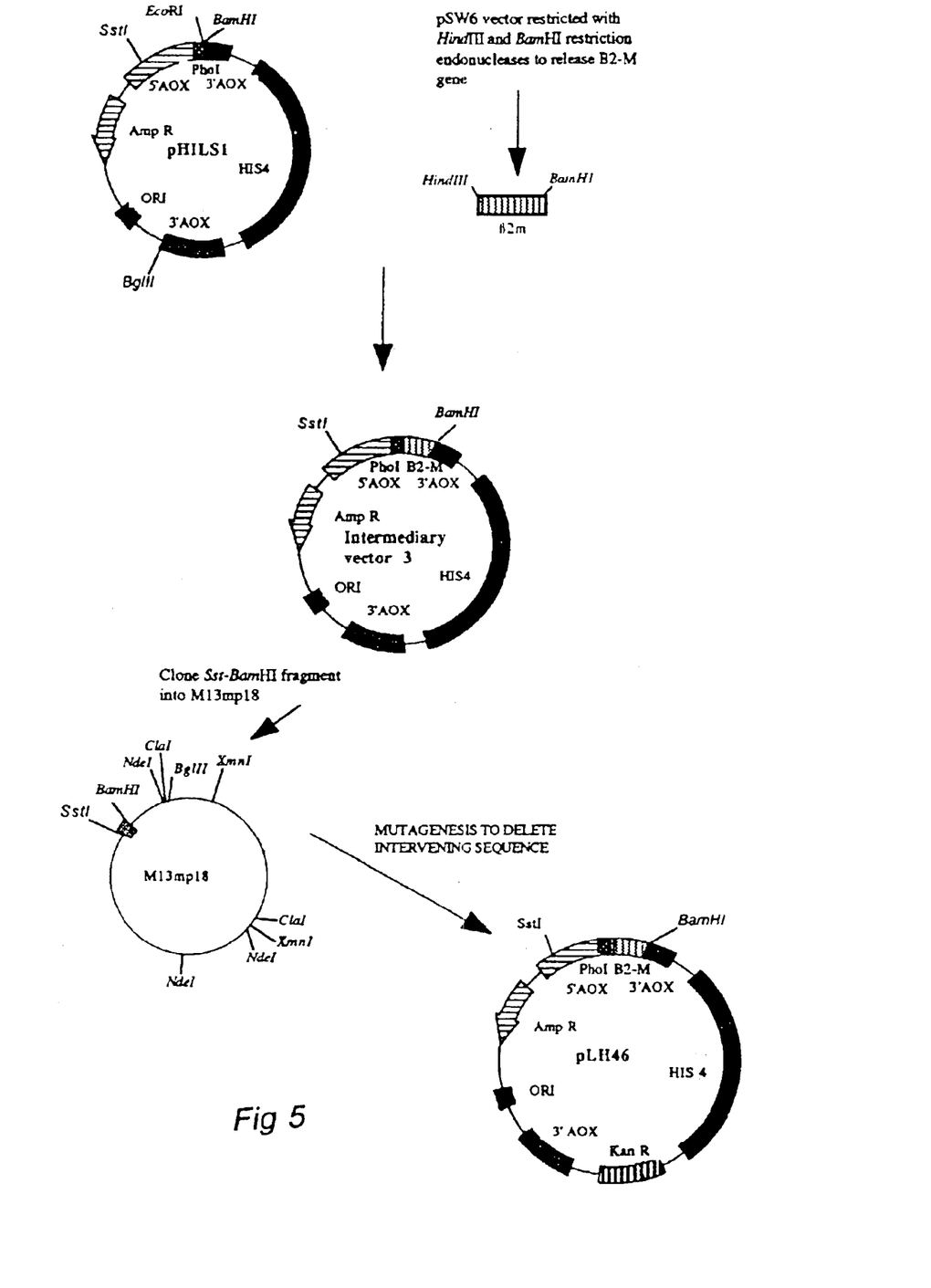
FIG. 5 shows the *Pichia* expression vector pHILS1 used as the starting point in example 4 for the construction of the expression vector for high-level expression of B2M in *P.pastoris*, using the Pho1 leader sequence, and the manipulations leading to the final *P. pastoris* Pho1/B2M expression vector pLH46 according to example 4.
Figure 6:
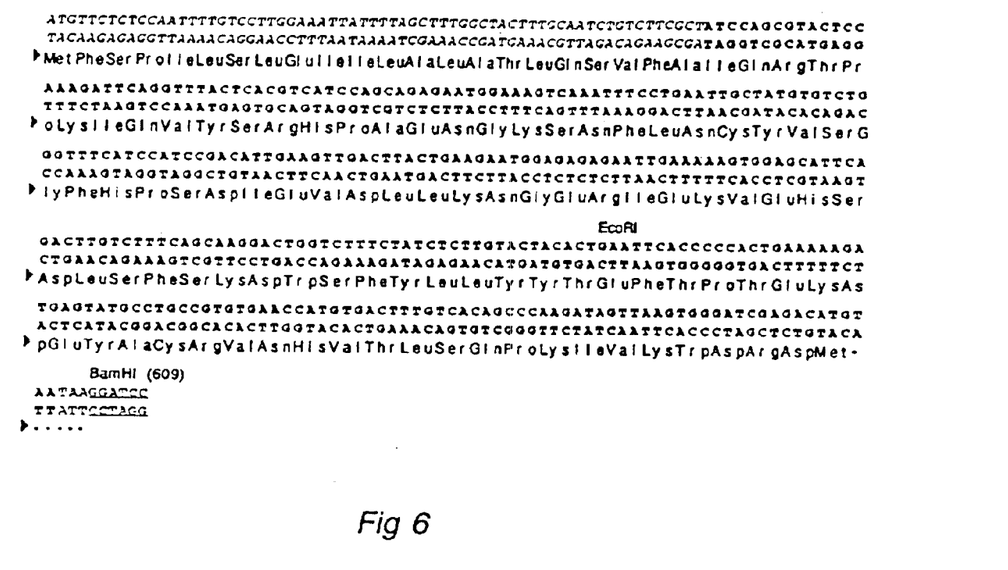
FIG. 6 shows the sequence of the Pho1/B2M fusion included in pLH46 (FIG. 5) (nucleic acid sequence, SEQ ID 23; amino acid sequence SEQ ID 33), where the underlined sequence represents the cloning site, the italics represent the Pho1 signal sequence, and the bold letters are identical to the sequence of the B2M gene.

The cDNA was then amplified in PCR reactions using primer (5'-GACAAGCTTGGATAAAAGAATCCAGCGT-ACTCCAAAG-3') SEQ ID 1 to add a HindIII restriction site and an adaptor sequence encoding the last 5 amino acids of the *S.cerevisiae* alpha mating factor at the 5' end of the gene, and (5'-CATAGGATCCTTATTACATGTCTCGATCCCA-CTT-3') SEQ ID 2 that added a termination codon and a BamH1 site at the 3' end of the gene. PCR products were generated in 30 cycles of denaturation at 97° C. for 1 min, annealing at 60° C. for 1 min and elongation 72° C. for 30 seconds. The reactions were carried out in 1 mM MgCl2, 50mM KCl, 10 mM Tris pH 8.3 using 50 ng of primer in a volume of 50 µl. The sequence of the gene is shown in FIG. 2. After PCR amplification the DNA was digested with HindIII and BamH1 and ligated into HindIII-BamHI calf intestinal phosphatase-treated M13mp19.M13 clones were then sequenced to identify isolates that had no difference to the published sequence using universal primer (5'-GTTTTCCCAGTCACGAC-3') SEQ ID 3. DNA was then purified from one of these clones and subcloned into the *S.cerevisiae* expression vector pSW6 (see Example 2).

EXAMPLE 2

Cloning the Beta-2-Microglobulin Gene into the *S.cerevisiae* Expression Vector pSW6

An expression vector was designed to enable secretion of B2 microglobulin to the extracellular medium after expression in *S. cerevisiae*. Secretion aids purification and rapid analysis of B2M. The secretion signals from the yeast mating type factor alpha were used to direct export of the B2 microglobulin protein.

Figure 1:
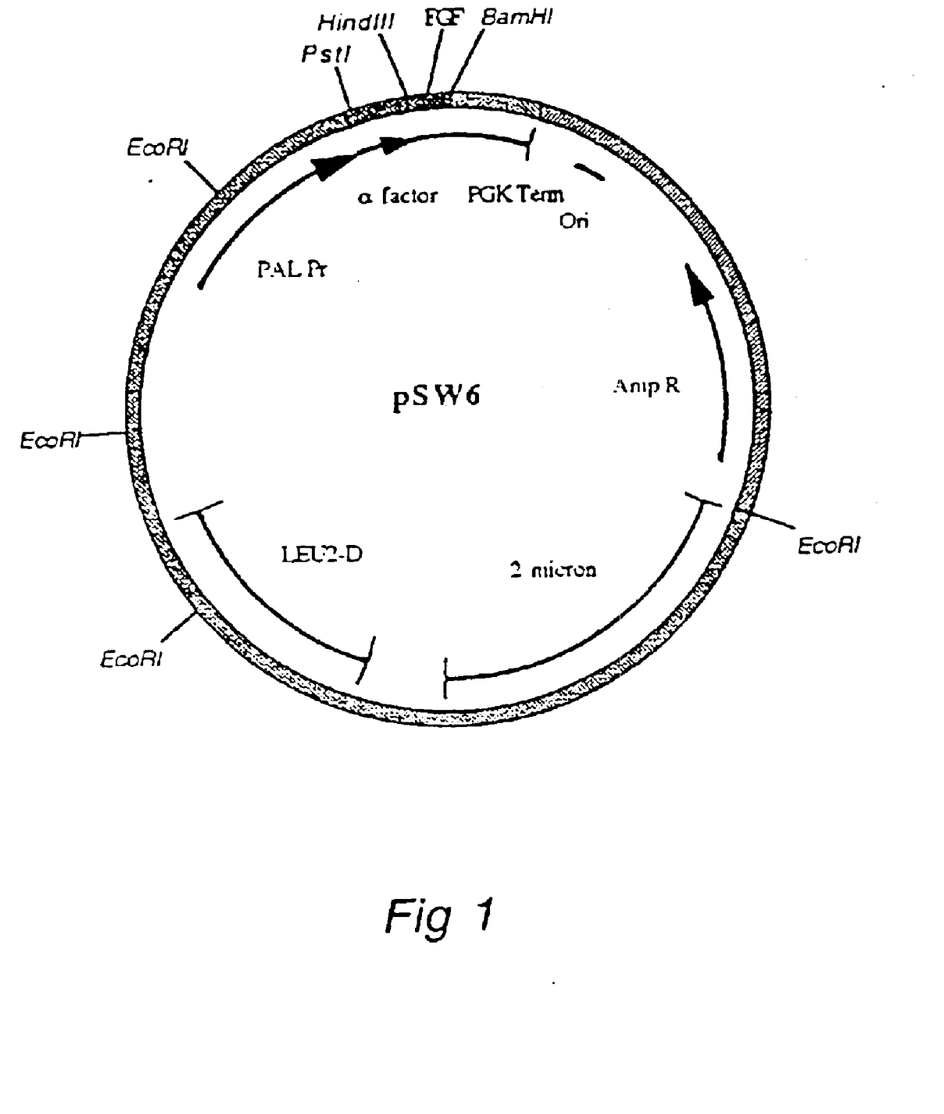
FIG. 1 shows the yeast expression vector pSW6, into which is cloned the B2M gene according to example 2.

The yeast expression vector pSW6 (FIG. 1) is based on the 2 micron circle from *S. cerevisiae*. (pSW6 is deposited in *S. cerevisiae* strain BJ2168 at the National Collection of Industrial and Marine Bacteria Limited, 23 St. Machar Drive, Aberdeen AB2 1 RY, United Kingdom under Accession No. NCIMB 40326). pSW6 is a shuttle vector capable of replication in both *E. coli* and *S. cerevisiae* and contains an origin of DNA replication for both organisms, the leu2 gene (a selectable marker for plasmid maintenance in the yeast host) and the ampicillin resistance locus for selection of plasmid maintenance in *E. coli*. (The DNA sequence for the vector is disclosed in WO-A-09125). The ability to passage this vector through *E. coil* greatly facilitates its genetic manipulation and ease of purification. pSW6 contains an alpha-factor pre-pro-peptide gene fused in-frame to a gene encoding human epidermal growth factor (EGF). The expression of this fusion is under the control of an efficient galactose regulated promoter which contains hybrid DNA sequences from the *S. cerevisiae* GAL 1–10 and phosophoglycerate kinase (PGK) promoters. Transcription of the EGF gene is terminated in this vector by the natural yeast PGK terminator. The EGF gene in pSW6 can be removed by digestion with restriction endonucleases HindIII and BamHI. This removes DNA encoding both EGF and 5 amino acids from the C-terminus of the alpha-factor propeptide. Genes to be inserted into the pSW6 expression vector must therefore have the general composition: HindIII site-alpha factor adaptor-gene-BamHI site. The B2M gene prepared in Example 1 has this general composition.

After digestion with HindIII and BamHI endonucleases, the pSW6 vector contains the alpha factor gene minus the codons for the last five amino acid residues. The B2M gene prepared as in Example 1 was then cloned into the pSW6 vector. The resulting vector was then transformed into the host strain BJ2168 using the method of Ito et al J. Bacteriol. (1983)153 163–168.

EXAMPLE 3

Construction of Alpha Factor/B2M *Pichia Pastoris* Expression Vector

The expression vectors used for this work were derived from the Phillips Petroleum expression vector pHILD1.

*Pichia* expression vector pHILD1 (FIG. 2) is a shuttle vector capable of propagation in both *E. coli* (for ease of genetic manipulation) and in the methylotrophic yeast *Pichia pastoris*. pHILD1 can be obtained under licence from the Phillips Petroleum Company, Bartlesville Okla., USA. The vector comprises sequences derived from the *E.coli* vector pBR322 and sequences derived from the genome of *Pichia pastoris*. The essential features are the 5' region of the *Pichia* AOX gene including the regulatable AOX promoter for high level transcription, the 3' region from the AOX gene containing the alcohol oxidase transcriptional terminator sequence, a further region from the 3' part of the ~AOX gene is included which together with the 5' AOX region is required for site directed integration of the expression cassette into the host genome. The *P. pastoris* histidinol dehydrogenase gene HIS4 is carried and used to complement the defective HIS 4 gene in *Pichia* host strains. The ampicillin resistance gene is carried to enable selection in the *E.coli* hosts used during genetic manipulation.

The pHILD1 vector was manipulated to allow expression of the B2M gene under the control of the alpha factor secretion signal. pHILD1 does not carry any sequences encoding secretion signals to allow export of heterologous proteins. To include such a signal, the vector was manipulated by the addition of sequences from the *S.cerevisiae* alpha factor leader. The vector was further engineered to provide a more optimal promoter context and to remove undesirable Hind III restriction sites which may interfere with the cloning of the B2M gene, a Bam HI site was then introduced 3' to the remaining Hind III to allow cloning of the B2M gene on a HindIII—BamHI restriction site and to include a kanamycin resistance cassette enabling the selection of multicopy integrants in transformed *Pichia* host strains. The stages of the manipulations are shown below.

1) Inclusion of Alpha Factor Secretion Signals

The alpha factor sequences were cloned into the pHILD1 vector from the *S. cerevisiae* expression vector pSW6 (FIG. 1) (see example 2 for details). The alpha factor sequences were isolated from pSW6 on ca 430 bp Bgl II-Bam HI DNA fragment, this fragment contains the alpha factor sequences fused to a human epidermal growth factor synthetic gene (EGF). The overhanging ends of this DNA fragment were first filled in using klenow fragment of *E.coli* DNA polymerase I together with the required deoxynucleoside triphosphates according to standard methodology. The flush ended fragment was then cloned into the pHILD1 vector that had been treated with Eco RI and then blunt ended as above. The integrity of the resultant plasmid pLH001 was checked by a combination of restiction digestion and DNA sequence analysis. The primer use for sequence analysis was (5'-GCATTCTGACATCCTCT-3'), SEQ ID 4. The sequence of the alpha factor fusion was confirmed.

2) Mutagenesis to Optimise Vector for B2M Expression

To remove unwanted Hind III restriction sites, optimise the promoter region and introduce a Bam H1 site from the pLHOO1 vector, relevant fragments were cloned into bacteriophage M13 for site directed mutagenesis. The fragments cloned, the primers used for mutagenesis, and the primers used for sequencing are detailed below. Furthermore, a kanamycin resistance cassette was modified for introduction into the final expression vector to allow selection for muticopy integrants when the vector is introduced into *Pichia* host strains.

A 1220 bp SacI-SacI fragment was isolated from pLH001 and cloned into M13 mp19. This M13 construct was then used for mutagenesis in which a Hind III site was removed using oligonucleotide primer (5'-CGTTAAAATCAACAACTTGTCAATTG-GAACC-3'), SEQ ID 5, the mutants were identified by sequence analysis with sequencing primer (5'-GGAAATCTCACAGATCT-3'), SEQ ID 6. This fragment was further modified by deletion mutagenesis to optimise the 5' untranslated leader region preceeding the AOX promoter, which is now identical to that found in the natural 5' untranslated leader of the AOX1 gene on the *Pichia* genome. Having the correct context around the 5' untranslated leader is preferred for maximal expression. The mutagenesis primer used for this step was (5'GAAGGAAATCTCATCGTTTCGAATA-3'), SEQ ID 7. The mutant was identified by sequence analysis with sequencing primer (5'-GCTAATGCGG-AGGATGC-3'), SEQ ID 8.

Two further Hind III sites was removed from from the 770 bp Sac I-Xba I fragment of pLH001 by mutagenesis. The SacI-XbaI fragment of pLH001 was first cloned into M13 mp18 and one of the Hind III sites was removed using the primer (5'-CCGGCATTACAACTTATCGATAAGCTTGCAC-3'), SEQ ID 9. The identity of this mutant was confirmed by sequence analysis using the sequencing primer (5'-GCGCATTGTTAGATTTC-3'), SEQ ID 10. A second HindIII site was removed from this newly mutagenised fragment using mutagenesis primer (5'-CTTATCGATCAACTTGCACAAACG-3'), SEQ ID 11. The correct mutant was identified by sequence analysis using sequence primer SEQ ID 9 (see above).

Before reassembly, a Bam HI site was introduced into the Hind III deleted Sac I-Xba I fragment to allow subsequent cloning of the B2M gene of example 1 on a Hind III-Bam HI fragment. The mutagenesis primer used to introduce the Bam H1 site was (5'-GTCATGTCTAAGGCGGATCCTTATTAAC-3'), SEQ ID 12. The identity of the mutant was identified using sequencing primer (5'-GCATTCTGACATCCTCT-3') SEQ ID 13.

3) Modification of the Kanamycin Resistance Cassette

A kanamycin resistance cassette was purchased from Pharmacia Biosystems Limited, Davy Avenue. Knowlhill, Milton Keynes, MK5 8PH. Great Britain. This cassette is supplied as an EcoRI fragment by Pharmacia and this was cloned into M13 mp19 as an EcoR1 fragment. The internal Hind III was deleted using mutagenesis primer (5'-GAGAATGGCAACAACTTATGCATT-3'), SEQ ID 14. The mutation was confirmed using sequencing primer (5'-CCAACATCAATACAACC-3'), SEQ ID 15.

4) Reassembly of Expression Vector

The vector was reconstructed in a stepwise manner using the Phillips petroleum vector pHILD1 as a backbone for the cloning.

To rebuild the expression vector including the mutagenised fragments, the modified ca 770 bp SacI-XbaI fragment was first ligated into SacI -XbaI treated pHILD1 vector. The integrity of the recombinant construct was then confirmed by restriction analysis and DNA sequence analysis using the oligonucleotide sequencing primer (5'-GCGCATTGTTAGATTTC-3'), SEQ ID 16, the construct was called intermediary vector 1. The modified Sac I-Sac I fragment was next cloned into intermediary vector 1 which had been treated with Sac I and calf intestinal phosphatase. The resultant construct named intermediary vector 2, was again confirmed by restriction analysis and DNA sequence analysis with oligonucleotide primers (5'-GGAAATCTCATAGATCT-3'), SEQ ID 17 to read through the deleted Hind III site and (5'-GCTAATGCGGAGGATGC-3'), SEQ ID 18 to read through the optimised 5' untranslated leader region. Intermediary vector 2 is a homologue of pHILD1 which lacks the unwanted Hind III sites, has an optimised 5' untranslated region, contains sequences encoding the *S. cerevisiae* alpha factor secretion signals followed by the remaining Hind III site and which has a Bam HI site 3' to the HindIII site to allow cloning of the B2M gene.

A 1200 bp Hinc11 fragment containing the mutagenised kanamycin cassette was removed from the M13 mp19 mutagenesis vector (used to remove the Hind III site from the kanamycin resistance gene) and cloned into the unique Nae 1 site of the intermediary vector 2. The vector was renamed pLHD4. The integrity of pLHD4 was confirmed by restriction analysis. A map of pLHD4 is shown in FIG. 3. pLHD4 contains the human EGF gene fused to the *S. cerevisiae* secretion signal.

5) Construction of the B2M *Pichia* Expression Vector

The final expression vector for B2 microglobulin expression was constructed by cloning the Hind III-Bam HI fragment of example 2 into pLHD4. (This 320 bpHind III-Bam HI fragment contains the B2M gene fused to the 3' end of a sequence encoding the 5 amino acids of the yeast alpha factor which precede the KEX2 cleavage site required for liberation of the mature peptide following secretion from the *Pichia* host).

The Hind III-Bam H1 fragment was obtained by restriction digestion of the *S. cerevisiae* expression vector pSW6 B2M. This fragment was purified on a 1.5% low melting temperature agarose gel then ligated to Hind III-Bam H1, calf intestinal phosphatase treated pLHD4. The resultant recombinant was called pLH15. The vector is shown on FIG. 4. (At this time the Kanamycin resistance gene was defective, due to a then unknown deletion of bases, which occured during mutagenesis to delete the internal Hindl III site. A ca 2070 bp SacI-Xba I fragment was removed from the resultant construct and cloned into the expression vector pHILD4, so conferring Kanamycin resistance) The integrity of the construct was confirmed by restriction analysis and sequencing analysis using the sequencing primer (5'-GCATTCTGACATCCTCT-3'), SEQ ID 19.

EXAMPLE 4

Construction of Pho1/B2M *Pichia Pastoris* Expression Vector

The expression vectors used for this work were derived from the Phillips Petroleum expression vector pHILS1 (FIG. 5)

The starting expression vector for manipulation was the *Pichia pastoris* shuttle vector pHILSI (obtainable under licence from Phillips Petroleum) capable of propagation in both *E. coli* (for ease of genetic manipulation) and in the methylotropic yeast *Pichia pastoris*. It contains the Pho1 leader sequence from the *Pichia pastoris* acid phosphatase gene. It also contains sequences from the *E. coli* vector pBR322 and sequences derived from the genome of *Pichia pastoris*. The essential features are the 5' region of the AOX gene including the methanol regulatable AOX promoter for high level transcription, the 3' region from the AOX gene containing the alcohol oxidase transcriptional terminator sequence, a further region from the 3' region which together with the 5'AOX region is required for site directed integration into the expression cassette into the chromosome. The *Pichia* histidinol dehydrogenase gene HIS4 is carried and used to complement the defective copy of the his4 gene on the host genome. The ampicillin resistance gene is carried to enable selection in the *E. coli* host used during the genetic manipulation.

The pHILS1 vector was manipulated to allow expression of the B2M gene under the control of the Pho1 secretion signal:

The gene encoding B2M was cloned into the pHILS1 vector from the *S. cerevisiae* expression vector pSW6 containing the gene as a HindIII-BamHI fragment (Example 2). The overhanging end of the DNA fragment at the HindIII site was first filled in to create a blunt end using the Klenow fragment of DNA polymerase I together with the required deoxynucleotide triphosphates according to standard methodology. The vector pHILSI was restricted with restriction endonucleases EcoR1 and Bam H1. The overhanging end of the DNA fragment at the EcoR1 site was filled in as described above to create a blunt end. The B2M gene, as a blunt end BamHI site was cloned into the blunt end BamHI treated vector. The integrity of the resultant vector, intermediary vector 3, was confirmed by restriction analysis.

The HindIII-BamHI fragment from the expression vector pSW6 contains the B2M gene fused at the 3' end to the last 5 amino acids of the yeast alpha factor which precedes the KEX2 cleavage site required for liberation of the mature peptide following secretion from the *Pichia pastoris* host when using the alpha factor sequence. This sequence and a few bases at the cloning site were deleted to allow the direct fusion of the Pho1 leader sequence and the B2M gene. The sequence deleted is (5'-CGAGAATTAGCTTGGATAAAAGA-3'), SEQ ID 20.

A ca 1150 bp (SstI) SacI-BamHI fragment was isolated from the intermediary vector 3 and cloned into the vector M13mpl8. This fragment contains 700 bp of the 5' AOX promoter sequence, Pho1 signal sequence and the B2M gene. The M13 construct was then used for mutagenesis to delete the intervening sequence between the Pho1 sequence and the B2M gene. The oligonucleotide primer used for mutagenesis was (5'-GGAGTACGCTGGATAGCGAAGACAGATTG-3') SEQ ID 21. The mutants were identified by sequence analysis using the sequencing primer (5'-CCATTCTCTGCTGGATG-3') SEQ ID 22. The sequence of Pho1/B2M is shown in FIG. 6, SEQ ID 23

The vector was reconstructed using the expression vector pLH15 (Example 3(5)) as a backbone for the cloning. The vector was restricted with the restriction endonucleases (Sst) SacI and BamHI to release a ca 1150 bp fragment containing a 700 bp fragment of the 5' AOX promoter sequence and alpha factor signal sequence fused to the B2M gene, which was then replaced by the mutagenised (Sst) SacI-BamHI fragment containing a 700 bp fragment of the 5' AOX promoter sequence, Pho1 signal sequence fused to the B2M gene. The resultant recombinant was called pLH46. The vector is shown on FIG. 6. The integrity of the construct was confirmed by restriction analysis using the sequencing primer (5'-GCATTCTGACATCCTCT-3') SEQ ID 24.

EXAMPLE 5

Construction of Vectors pGC633 Containing the DNA Sequence of the Sendai Virus Epitope The expression vector pGC633 contains the gene encoding B2M fused at the 5' end to the Sendai virus epitope (Kast et al Proc. Natl. Acad. Sci. 88, 2283–2287 (1991)) via a short linker. The epitope/linker peptide sequence fused to the B2M sequence is FAPGNYPAL<u>GGGGG</u>, SEQ ID 25. The underlined amino acids constitute the linker sequence, designed to span the gap between the peptide and the B2M with minimal disruption to the conformation of the light chain.

The expression vector pLH46 (Example 3) was restricted with the restriction endonucleases SacI (SstI) and BamHI to release a ca 1150 bp fragment containing a 700 bp fragment of the 5' AOX promoter sequence, Pho1 signal sequence fused to the B2M gene. This fragment was cloned into M13mp18 which had been restricted with SacI (SstI) and BamHI. The M13 construct was then used for mutagenesis to insert the sequence encoding the Sendai peptide. The oligonucleotide primer used for mutagenesis was (5'-GGAGTACGCTGGATACCACCACCACCAC-CCAAAGCTGGGTAGTTACCTGGAGC GAAAGCGAAGACAGATT-3'), SEQ ID 26. The mutants were identified by sequence analysis using sequencing primer (5'-CCATTCTCTGCTGGATG-3'), SEQ ID 27.

The vector was reconstructed using the expression vector pLH46 (Example 3) as a backbone for the cloning. The vector was restricted with the restriction endonucleases SacI (SstI) and BamHI to release a ca 1150 bp fragment containing a 700 bp fragment of the 5' AOX promoter sequence, Pho1 signal sequence fused to the B2M gene, and replaced with the mutagenised fragment. The integrity of the construct was confirmed by restriction analysis and sequencing analysis using the sequencing primer (5'-GCATTCTGACATCCTCT-3'), SEQ ID 28.

EXAMPLE 6

Construction of Vectors pGC638 Containing the DNA Sequence of the Influenza A Virus Epitope the expression vector pGC638 contains the gene encoding B2M fused at the 5' end to the influenza virus epitope (Current Biology, 3 No. 12 1993). The epitope/linker peptide sequence fused to the B2M sequence is GILGFVFTLG GGGGGSSS, SEQ ID 29. The underlined amino acids constitute the linker sequence, designed to span the gap between the peptide and the B2M with minimal disruption to the conformation of the light chain.

The expression vector pLH46 (Example 3) was restricted with the restriction endonucleases SacI (SstI) and BamHI to release a ca 1150 bp fragment containing a 700 bp fragment of the 5' AOX promoter sequence, Pho1 signal sequence fused to the B2M gene. This fragment was cloned into M13mp18 which had been restricted with SacI (SstI) and BamHI. The M13 construct was then used for mutagenesis to insert the sequence encoding the Sendai peptide. The oligonucleotide primer used for mutagenesis was (5'-GGAGTACGCTGGATAGAAGAAGAACCAC-CACCACCACCACCCAAAGTGAAAAC GAAACCCAAAATACCAGCGAAGACAGATT-3'), SEQ ID 30. The mutants were identified by sequence analysis using sequencing primer (5'-CCATTCTCTGCTGGATG-3'), SEQ ID 27.

The vector was reconstructed using the expression vector pLH46 (Example 2) as a backbone for the cloning. The vector was restricted with the restriction endonucleases SacI (SstI) and BamHI to release a ca 1150 bp fragment containing a 700 bp fragment of the 5' AOX promoter sequence, Pho1 signal sequence fused to the B2M gene, and replaced with the mutagenised fragment. The integrity of the construct was confirmed by restriction analysis and sequencing analysis using the sequencing primer (5'-GCATTCTGACATCCTCT-3'), SEQ ID 31.

EXAMPLE 7

Construction of Pichia Expression Strains

DNA of each of plasmids pGC633 and pGC638 (Examples 4 and 5) was linearised by cutting with the restriction endonuclease SacI. This was to enable the expression cassette to integrate via homologous recombination of sequences on the expression cassette and the host chromosome. In each case, the linearized plasmid was then transformed into P.pastoris strain GS115 (NRRL Y-1585) which has the genotype his 4. The use of this strain is not critical for use either in this preparation or in the invention in general. Any suitable strain can be used, such as, for example, strains SMD1163 and and KM71 which have the genotypes his4, prB1, pep4 and his4, aox1::SARG4. Strains GS115 and KM71 are described in Phillips patent number AU-B-63882/86 (Site selective genomic modification of yeast of the genus Pichia).

The plasmids were linearized with SacI and used to transform the host strain. Yeast strain GS115 was grown overnight in 200 ml YEPD at 30° C. in an orbital shaker. Cultures at an A600 of between 1.3–1.5 were harvested by centrifugation at 3000 rpm for 5 min, washed in ice cold sterile water, recentrifuged and resuspended in 8 ml ice cold 1 M sorbitol. 40 µl cells were added to 1 µg linearized DNA in an ice cold 0.2 cm electroporation cuvette. After 5 min on ice the cells were pulsed using the BioRad gene pulser unit at 25 µF, 1.5 kV, and 400 Ohm. 1 ml ice cold 1M sorbitol was added to the cuvette. 400 µl of this was plated onto agarose plates and allowed to grow for 2–4 days at 30° C.

All yeast media and transformation buffers were as described in the appendix.

Transformants were collected along with the agarose overlay they had been growing in, transferred to a 50 mL centrifuge tube and resuspended in 50 mM sodium phosphate buffer pH6. After suitable mixing and agitation to remove the cells from the agarose they were diluted and plated onto YEPD agar plates containing the antibiotic G418 at concentrations between 0 and 2000 µg/mL. Only cells in which several copies of the expresssion cassette had integrated onto the host chromosome would be able to grow on high levels of antibiotic by virtue of the several copies of the kanamycin resistance gene they would be carrying. Such cells are deemed desirable since they will also be carrying several copies of the B2M gene. Previous work has shown such multicopy integrants to be high producers under conditions were the foreign gene is expressed (Clare, J. J., Rayment, F. B., Ballantine, S. P., Sreekrishna, K., and Romanos, M. A., BIO/TECHNOLOGY, 9, 455–460,1991). Plates were incubated at 30° C. for 5–7 days. Colonies occuring on plates containing high concentrations of the antibiotic were then picked and streaked onto fresh MD agar plates. Single colonies were obtained after 3–4 days growth at 30° C.

EXAMPLE 8

Expression of Hybrid Sendai/B2M and Influenza/B2M Fusion Proteins in P.Pastoris

In separate experiments, single colonies of transformed strains harbouring pGC633 and (separately) pGC638 were used to inoculate 5 mL of BMGC medium and the cultures were grown overnight at 30° C. on an orbital shaker. This 5 mL overnight culture was then used to inoculate 2 L baffled shake flasks containing 50 mL of the medium BMGC. After 24 h growth at 30° C. on an orbital incubator cells were harvested by centrifugation at 3000 rpm for 5 mins and resuspended in 50 mL of BMMC. This induces gene expression from the AOX1 promoter. Induction was carried out by growth in the methanol containing medium at 30° C. for 48 hours. After 24 hours 250 µL of sterile methanol are added to the flask to replace that lost by evaporation.

After 48 hours the culture supernatant was collected by centrifugation at 3000 rpm for 5 min. The supernatent was used for further analysis. Production levels from strains with the alpha factor leader sequence were estimated by SDS-PAGE to be in the order of 150 mg/L.

EXAMPLE 9

Induction of Sendai NP-specific Cytotoxic T-Lymphocytes (CTL) by the Hybrid Sendai/B2M Product of Example 7 (pGC633)

C57BU6 (H-2b) mice were immunized subcutaneously with either 50, 10, 2 or 0.4 μg of the hbrid Sendai NP-B2 M fusion protein expressed by pGC633 according to example 7, or 50 μg of B2M plus 20 ng of the Sendai NP epitope (FAPGNYPAL)—part of SEQ ID 9. After 6 days the spleens were removed from two mice per group and a single cell suspension prepared which was restimulated in vitro with the Sendai NP peptide. After 24 hours 2% of an IL2 preparation was added. Following 7 days restimulation in vitro these effector cells were tested for their ability to lyse Sendai NP peptide-pulsed EL4 (H-$2^b$) target cells. The ratios of effector (E) to target (T) cells were 100:1, 33.3:1. 11.1:1 and 3.7:1. The results of this test were recorded as % net specific lysis, which is calculated by subtracting the lysis of non-peptide-pulsed targets from that obtained using peptide-pulsed targets.

Figure 7:
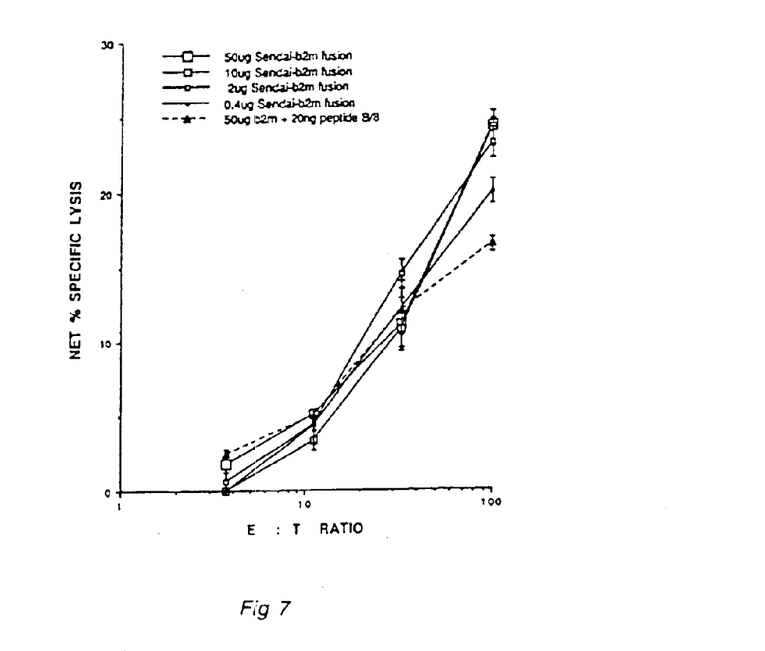
FIG. 7 shows the resut of the test described in Example 9.

The results are plotted in FIG. 7. A peptide-specific lysis of 24.4% was seen at an ET ratio of 100:1 following immunization with 50 μg of the fusion protein. All immunisation doses of the fusion protein gave responses similar to those obtained by immunising with a mixture of B2M and Sendai NP peptide

| Media recipies | |
| --- | --- |
| BMGC | |
| Quantities per liter: | |
| Sodium phosphate buffer 1M, pH6 | 100 mL |
| Casamino acids (100 g/L) | 100 mL |
| Yeast Nitrogen Base (13.4 g/L) | 100 mL |
| Biotin (0.5 g/L) | 2 mL |
| Glycerol | 10 mL |
| Filter sterilise | |
| BMMC | |
| As above but replace glycerol with 5 mL of methanol. | |
| YEPD | |
| Yeast extract | 10 g/L |
| Peptone | 20 g/L |
| Glucose | 10 g/L |
| For solid medium add 15 g/L agar. | |
| Autoclave at 121° C. 15 min. | |

What is claimed is:

1. A hybrid fusion protein comprising a first amino acid sequence which is an antigenic cytolytic T lymphocyte (CTL) epitope, the first sequence being fused through an amino acid linker sequence to a second amino acid sequence which binds to class I major histocompatibility complex (MHC) molecules, said second sequence being selected from the group consisting of a beta-2 microglobulin (B2M) having an amino acid sequence identical to a naturally occurring B2M and B2M having an amino acid sequence that has at least 95% amino acid sequence identity with the amino acid sequence of a naturally occurring B2M, wherein the second sequence has the B2M ability to augment the immune response to the first amino acid sequence.

2. A pharmaceutical or veterinary composition comprising the hybrid fusion protein as claimed in claim 1, together with a pharmaceutically acceptable carrier.

3. A hybrid fusion protein consisting of a first amino acid sequence which is an antigenic cytolytic T lymphocyte (CTL) epitope, the first sequence being fused through an amino acid linker sequence to a second amino acid sequence which binds to class I major histocompatibility complex (MHC) molecules, said second sequence being selected from the group consisting of a beta-2 microglobulin (B2M) having an amino acid sequence identical to a naturally occurring B2M and B2M having an amino acid sequence that has at least 95% amino acid sequence identity with the amino acid sequence of a naturally occurring B2M, wherein the second sequence has the B2M ability to augment the immune response to the first amino acid sequence.

4. A hybrid fusion protein capable of forming a complex with alpha subunits of MHC class I molecules, comprising a first amino acid sequence which is an antigenic cytolytic T lymphocyte (CTL) epitope, wherein the first sequence is capable of binding to the alpha subunit of the major histocompatibility complex (MHC) class I molecules, said first sequence being fused through an amino acid linker sequence to a second amino acid sequence, which binds to class I MHC molecules, said second sequence being selected from the group consisting of a beta-2 microglobulin (B2M) having an amino acid sequence identical to a naturally occurring B2M, and B2M having an amino acid sequence that has at least 95% amino acid sequence identity with the amino acid sequence of a naturally occurring B2M, wherein the second sequence has the B2M ability to augment the immune response to the first amino acid sequence.

5. The hybrid fusion protein of claim 1 wherein the second amino acid sequence comprises the amino acid sequence identical to a naturally occurring B2M.

6. The hybrid fusion protein of claim 1 wherein the first amino acid sequence comprises the antigenic CTL epitope of a proteinaceous human tumor antigen, an epithelial-tumor associated antigen, a virus, a bacterium, a fungus, or a parasite.

7. The hybrid fusion protein of claim 6 wherein the virus is selected from the group consisting of human immunodeficiency virus type-1, human immunodeficiency virus type-2, human T-cell leukemia virus type-1, human T-cell leukemia virus type-2, human T-cell leukemia virus type-3, simian immunodeficiency virus, bovine immunodeficiency virus, lymphadenopathy associated virus, equine infectious anemia virus, chicken infectious anemia virus, murine leukemia virus, Moloney murine leukemia virus, feline leukemia virus, influenza A, influenza B, parainfluenza virus, mumps, measles, Rous sarcoma virus, Sendai virus, human papilloma virus, lymphocytic choriomeningitis virus, hepatitis B virus, herpes simplex virus, varicella zoster virus, cytomegalovirus, and Epstein Barr virus.

8. The hybrid fusion protein of claim 6 wherein the bacterium is from a genus selected from the group consisting of *Neisseria, Campylobacter, Bordetella, Listeria, Mycobacteria* and *Leishmania*.

9. The hybrid fusion protein of claim 6 wherein the parasite is from a genus selected from the group consisting of *Trypanosoma, Schizosoma,* and *Plasmodium*.

10. The hybrid fusion protein of claim 6 wherein the fungus is from a genus selected from the group consisting of *Candida, Aspergillus, Cryptococcus, Histoplasma,* and *Blastomyces*.

11. The hybrid fusion protein of claim 6 wherein the antigenic CTL epitope is of a proteinaceous human tumor antigen, or an epithelial-tumor associated antigen.

12. The hybrid fusion protein of claim 6 wherein the antigenic CTL epitope is an epitope derived from the group consisting of human immunodeficiency virus type-1 gp120, human immunodeficiency virus type-1 p24, varicella zoster virus gpI, varicella zoster virus gpII, varicella zoster virus gpIII, lymphocytic choriomeningitis virus nucleoprotein, human papilloma virus E5, human papilloma virus E7, malaria CSP antigen, malaria RESA antigen, mycobacterium p6, epithelial tumor-associated antigen GA 733-2, epithelial tumor-associated antigen MUC-1 repeat sequence, melanoma MZ2-E antigens, and melanoma p97 associated antigen.

13. The hybrid fusion protein of claim 1 wherein the first amino acid sequence is the antigenic CTL epitope of a third variable domain of an envelope protein of a lentivirus.

14. The hybrid fusion protein of claim 3 wherein the second amino acid sequence comprises the amino acid sequence identical to a naturally occurring B2M.

15. The hybrid fusion protein of claim 4 wherein the second amino acid sequence comprises the amino acid sequence identical to a naturally occurring B2M.

16. The hybrid fusion protein of claim 5 wherein the naturally occurring B2M has the amino acid sequence as shown in amino acid residues 23–121 of SEQ ID 33.

17. The hybrid fusion protein of claim 14 wherein the naturally occurring B2M has the amino acid sequence as shown in amino acid residues 23–121 of SEQ ID 33.

18. The hybrid fusion protein of claim 15 wherein the naturally occurring B2M has the amino acid sequence as shown in amino acid residues 23–121 of SEQ ID 33.

19. The hybrid fusion protein of claim 1 wherein the second amino acid sequence binds to the groove of the alpha subunit of the class I MHC molecules.

20. The hybrid fusion protein of claim 3 wherein the second amino acid sequence binds to the groove of the alpha subunit of the class I MHC molecules.

21. The hybrid fusion protein of claim 4 wherein the second amino acid sequence binds to the groove of the alpha subunit of the class I MHC molecules.

22. A hybrid fusion protein comprising a first amino acid sequence which is an antigenic cytolytic T lymphocyte epitope, the first sequence being fused through an amino acid linker sequence to a second amino acid sequence which binds to class I major histocompatibility complex molecules, said second sequence being a beta-2 microglobulin (B2M) having an amino acid sequence having at least 90% amino acid sequence identity with the amino acid sequence of a naturally occurring B2M, wherein the second sequence has the B2M ability to augment the immune response to the first amino acid.

23. A hybrid fusion protein consisting of a first amino acid sequence which is an antigenic cytolytic T lymphocyte epitope, the first sequence being fused through an amino acid linker sequence to a second amino acid sequence which binds to class I major histocompatibility complex molecules, said second sequence being a beta-2 microglobulin (B2M) having an amino acid sequence that has at least 90% amino acid sequence identity with the amino acid sequence of a naturally occurring B2M, wherein the second sequence has the B2M ability to augment the immune response to the first amino acid sequence.

24. A hybrid fusion protein capable of forming a complex with alpha subunits of major histocompatibility complex (MHC) class I molecules, comprising a first amino acid sequence which is an antigenic cytolytic T lymphocyte epitope, wherein the first sequence is capable of binding to the alpha subunit of the MHC class I molecules, said first sequence being fused through an amino acid linker sequence to a second amino acid sequence which binds to class I MHC molecules, said sequence being a beta-2 microglobulin (B2M) having an amino acid sequence that has at least 90% amino acid sequence identity with the amino acid sequence of a naturally occurring B2M.

* * * * *

UNITED STATES PATENT AND TRADEMARK OFFICE
CERTIFICATE OF CORRECTION

PATENT NO. : 6,881,828 B2  Page 1 of 1
DATED : April 19, 2005
INVENTOR(S) : Richard Mark Edwards et al.

It is certified that error appears in the above-identified patent and that said Letters Patent is hereby corrected as shown below:

<u>Title page,</u>
Item [56], References Cited, U.S. PATENT DOCUMENTS, insert
-- 4,478,823   10/1984   Sanderson --.
FOREIGN PATENT DOCUMENTS, insert
-- EP    0  448 095 A1   09/1991 --.
OTHER PUBLICATIONS, insert
-- Godeau et al., "Purification and ligand binding of a soluble class I major histocompatibility complex molecule consisting of the first three domains of H-2K d fused to beta 2-microglobulin..." The Journal of Biological Chemistry, 267: 24223-24229

Vedvick et al., "High-level secretion of biologically active aprotinin from the yeast Pichia pastoris", Journal of Industrial Microbiology, 7: 197-202. --.

Signed and Sealed this

Twenty-eighth Day of March, 2006

JON W. DUDAS
*Director of the United States Patent and Trademark Office*

SEQUENCE LISTING

```
<160> NUMBER OF SEQ ID NOS: 33

<210> SEQ ID NO 1
<211> LENGTH: 37
<212> TYPE: DNA
<213> ORGANISM: homo sapiens

<400> SEQUENCE: 1
gacaagcttg gataaaagaa tccagcgtac tccaaag                            37

<210> SEQ ID NO 2
<211> LENGTH: 34
<212> TYPE: DNA
<213> ORGANISM: homo sapiens

<400> SEQUENCE: 2
cataggatcc ttattacatg tctcgatccc actt                               34

<210> SEQ ID NO 3
<211> LENGTH: 17
<212> TYPE: DNA
<213> ORGANISM: homo sapiens

<400> SEQUENCE: 3
gttttcccag tcacgac                                                  17

<210> SEQ ID NO 4
<211> LENGTH: 17
<212> TYPE: DNA
<213> ORGANISM: homo sapiens
```

-continued

```
<400> SEQUENCE: 4
gcattctgac atcctct                                                17

<210> SEQ ID NO 5
<211> LENGTH: 31
<212> TYPE: DNA
<213> ORGANISM: homo sapiens

<400> SEQUENCE: 5
cgttaaaatc aacaacttgt caattggaac c                                31

<210> SEQ ID NO 6
<211> LENGTH: 17
<212> TYPE: DNA
<213> ORGANISM: homo sapiens

<400> SEQUENCE: 6
ggaaatctca cagatct                                                17

<210> SEQ ID NO 7
<211> LENGTH: 25
<212> TYPE: DNA
<213> ORGANISM: homo sapiens

<400> SEQUENCE: 7
gaaggaaatc tcatcgtttc gaata                                       25

<210> SEQ ID NO 8
<211> LENGTH: 17
<212> TYPE: DNA
<213> ORGANISM: homo sapiens

<400> SEQUENCE: 8
gctaatgcgg aggatgc                                                17

<210> SEQ ID NO 9
<211> LENGTH: 31
<212> TYPE: DNA
<213> ORGANISM: homo sapiens

<400> SEQUENCE: 9
ccggcattac aacttatcga taagcttgca c                                31

<210> SEQ ID NO 10
<211> LENGTH: 17
<212> TYPE: DNA
<213> ORGANISM: homo sapiens

<400> SEQUENCE: 10
gcgcattgtt agatttc                                                17

<210> SEQ ID NO 11
<211> LENGTH: 24
<212> TYPE: DNA
<213> ORGANISM: homo sapiens

<400> SEQUENCE: 11
cttatcgatc aacttgcaca aacg                                        24

<210> SEQ ID NO 12
<211> LENGTH: 28
<212> TYPE: DNA
<213> ORGANISM: homo sapiens
```

```
<400> SEQUENCE: 12
gtcatgtcta aggcggatcc ttattaac                              28

<210> SEQ ID NO 13
<211> LENGTH: 17
<212> TYPE: DNA
<213> ORGANISM: homo sapiens

<400> SEQUENCE: 13
gcattctgac atcctct                                          17

<210> SEQ ID NO 14
<211> LENGTH: 24
<212> TYPE: DNA
<213> ORGANISM: homo sapiens

<400> SEQUENCE: 14
gagaatggca acaacttatg catt                                  24

<210> SEQ ID NO 15
<211> LENGTH: 17
<212> TYPE: DNA
<213> ORGANISM: homo sapiens

<400> SEQUENCE: 15
ccaacatcaa tacaacc                                          17

<210> SEQ ID NO 16
<211> LENGTH: 17
<212> TYPE: DNA
<213> ORGANISM: homo sapiens

<400> SEQUENCE: 16
gcgcattgtt agatttc                                          17

<210> SEQ ID NO 17
<211> LENGTH: 17
<212> TYPE: DNA
<213> ORGANISM: homo sapiens

<400> SEQUENCE: 17
ggaaatctca tagatct                                          17

<210> SEQ ID NO 18
<211> LENGTH: 17
<212> TYPE: DNA
<213> ORGANISM: homo sapiens

<400> SEQUENCE: 18
gctaatgcgg aggatgc                                          17

<210> SEQ ID NO 19
<211> LENGTH: 17
<212> TYPE: DNA
<213> ORGANISM: homo sapiens

<400> SEQUENCE: 19
gcattctgac atcctct                                          17

<210> SEQ ID NO 20
<211> LENGTH: 23
<212> TYPE: DNA
<213> ORGANISM: homo sapiens
```

<210> SEQ ID NO 20

<400> SEQUENCE: 20
cgagaattag cttggataaa aga                                         23

<210> SEQ ID NO 21
<211> LENGTH: 29
<212> TYPE: DNA
<213> ORGANISM: homo sapiens

<400> SEQUENCE: 21
ggagtacgct ggatagcgaa gacagattg                                   29

<210> SEQ ID NO 22
<211> LENGTH: 17
<212> TYPE: DNA
<213> ORGANISM: homo sapiens

<400> SEQUENCE: 22
ccattctctg ctggatg                                                17

<210> SEQ ID NO 23
<211> LENGTH: 375
<212> TYPE: DNA
<213> ORGANISM: homo sapiens

<400> SEQUENCE: 23
atgttctctc caattttgtc cttggaaatt attttagctt tggctacttt gcaatctgtc    60
ttcgctatcc agcgtactcc aaagattcag gttactcac gtcatccagc agagaatgga   120
aagtcaaatt tcctgaattg ctatgtgtct gggtttcatc catccgacat tgaagttgac   180
ttactgaaga atggagagag aattgaaaaa gtggagcatt cagacttgtc tttcagcaag   240
gactggtctt tctatctctt gtactacact gaattcaccc ccactgaaaa agatgagtat   300
gcctgccgtg tgaaccatgt gactttgtca cagcccaaga tagttaagtg ggatcgagac   360
atgtaataag gatcc                                                   375

<210> SEQ ID NO 24
<211> LENGTH: 17
<212> TYPE: DNA
<213> ORGANISM: homo sapiens

<400> SEQUENCE: 24
gcattctgac atcctct                                                17

<210> SEQ ID NO 25
<211> LENGTH: 14
<212> TYPE: PRT
<213> ORGANISM: homo sapiens

<400> SEQUENCE: 25

Phe Ala Pro Gly Asn Tyr Pro Ala Leu Gly Gly Gly Gly Gly
1               5                   10

<210> SEQ ID NO 26
<211> LENGTH: 70
<212> TYPE: DNA
<213> ORGANISM: homo sapiens

<400> SEQUENCE: 26
ggagtacgct ggataccacc accaccaccc aaagctgggt agttacctgg agcgaaagcg    60
aagacagatt                                                         70

<210> SEQ ID NO 27
<211> LENGTH: 17
<212> TYPE: DNA
<213> ORGANISM: homo sapiens

<400> SEQUENCE: 27
ccattctctg ctggatg                                                       17

<210> SEQ ID NO 28
<211> LENGTH: 17
<212> TYPE: DNA
<213> ORGANISM: homo sapiens

<400> SEQUENCE: 28
gcattctgac atcctct                                                       17

<210> SEQ ID NO 29
<211> LENGTH: 18
<212> TYPE: PRT
<213> ORGANISM: homo sapiens

<400> SEQUENCE: 29

Gly Ile Leu Gly Phe Val Phe Thr Leu Gly Gly Gly Gly Gly Ser
1               5                   10                  15

Ser Ser

<210> SEQ ID NO 30
<211> LENGTH: 82
<212> TYPE: DNA
<213> ORGANISM: homo sapiens

<400> SEQUENCE: 30
ggagtacgct ggatagaaga agaaccacca ccaccaccac ccaaagtgaa acgaaaccc          60 aaaataccag cgaagacaga tt                                                 82

<210> SEQ ID NO 31
<211> LENGTH: 17
<212> TYPE: DNA
<213> ORGANISM: homo sapiens

<400> SEQUENCE: 31
gcattctgac atcctct                                                       17

<210> SEQ ID NO 32
<211> LENGTH: 9
<212> TYPE: PRT
<213> ORGANISM: homo sapiens

<400> SEQUENCE: 32

Phe Ala Pro Gly Asn Tyr Pro Ala Leu
1               5

<210> SEQ ID NO 33
<211> LENGTH: 121
<212> TYPE: PRT
<213> ORGANISM: homo sapiens

<400> SEQUENCE: 33

Met Phe Ser Pro Ile Leu Ser Leu Glu Ile Ile Leu Ala Leu Ala Thr
1               5                   10                  15

Leu Gln Ser Val Phe Ala Ile Gln Arg Thr Pro Lys Ile Gln Val Tyr
                20                  25                  30

-continued

```
Ser Arg His Pro Ala Glu Asn Gly Lys Ser Asn Phe Leu Asn Cys Tyr
        35                  40                  45

Val Ser Gly Phe His Pro Ser Asp Ile Glu Val Asp Leu Leu Lys Asn
    50                  55                  60

Gly Glu Arg Ile Glu Lys Val Glu His Ser Asp Leu Ser Phe Ser Lys
65                  70                  75                  80

Asp Trp Ser Phe Tyr Leu Leu Tyr Tyr Thr Glu Phe Thr Pro Thr Glu
                85                  90                  95

Lys Asp Glu Tyr Ala Cys Arg Val Asn His Val Thr Leu Ser Gln Pro
                100                 105                 110

Lys Ile Val Lys Trp Asp Arg Asp Met
            115                 120
```